United States Patent [19]
Melendez et al.

[11] Patent Number: 6,111,248
[45] Date of Patent: Aug. 29, 2000

[54] SELF-CONTAINED OPTICAL SENSOR SYSTEM

[75] Inventors: Jose L. Melendez, Plano; Richard A. Carr, Rowlett, both of Tex.

[73] Assignee: Texas Instruments Incorporated, Dallas, Tex.

[21] Appl. No.: 08/942,091

[22] Filed: Oct. 1, 1997

Related U.S. Application Data

[60] Provisional application No. 60/026,760, Oct. 1, 1996.

[51] Int. Cl.$^7$ .............................. G01N 21/00; H01J 3/14
[52] U.S. Cl. .............................. 250/239; 356/39; 356/73; 356/317
[58] Field of Search .................................... 250/216, 225, 250/227.11, 239; 356/39, 73, 317, 318, 445, 446, 448, 416, 417, 420, 364, 369

[56] References Cited

U.S. PATENT DOCUMENTS

| | | | |
|---|---|---|---|
| 5,299,141 | 3/1994 | Hungerford et al. | 364/510 |
| 5,485,277 | 1/1996 | Foster | 356/445 |
| 5,517,313 | 5/1996 | Colvin, Jr. | 356/417 |
| 5,898,503 | 4/1999 | Keller et al. | 356/445 |
| 5,912,456 | 6/1999 | Melendez et al. | 250/216 |
| 5,946,083 | 8/1999 | Melendez et al. | 356/73 |

OTHER PUBLICATIONS

Tokumitsu et al., "Three–Dimensional MMIC Technology: A Possible Solution to Masterslice MMIC's on GaAs and Si," *IEEE Microwave and Guided Wave Letters*, vol. 5, No. 11, Nov. 1995, pp. 411–413.

*Primary Examiner*—John R Lee
*Attorney, Agent, or Firm*—David Denker; Carlton H. Hoel; Frederick J. Telecky, Jr.

[57] ABSTRACT

A self-contained optical sensor (5) with a device platform (7) and an encapsulating light transmissive housing (9) formed therein is disclosed in conjunction with several sensor configurations including fluorescence-based, surface plasmon resonance based and light transmissive (bio) chemical sensor applications. The sensor (10) has at least one light source (20), a photodetector (25), a power source (18) and a display (50) which are embedded in an encapsulating housing (14). In other embodiments, a signal processing unit (35), converter circuit (30) and wireless Communications means (40, 45) are also included in the housing (14).

18 Claims, 3 Drawing Sheets

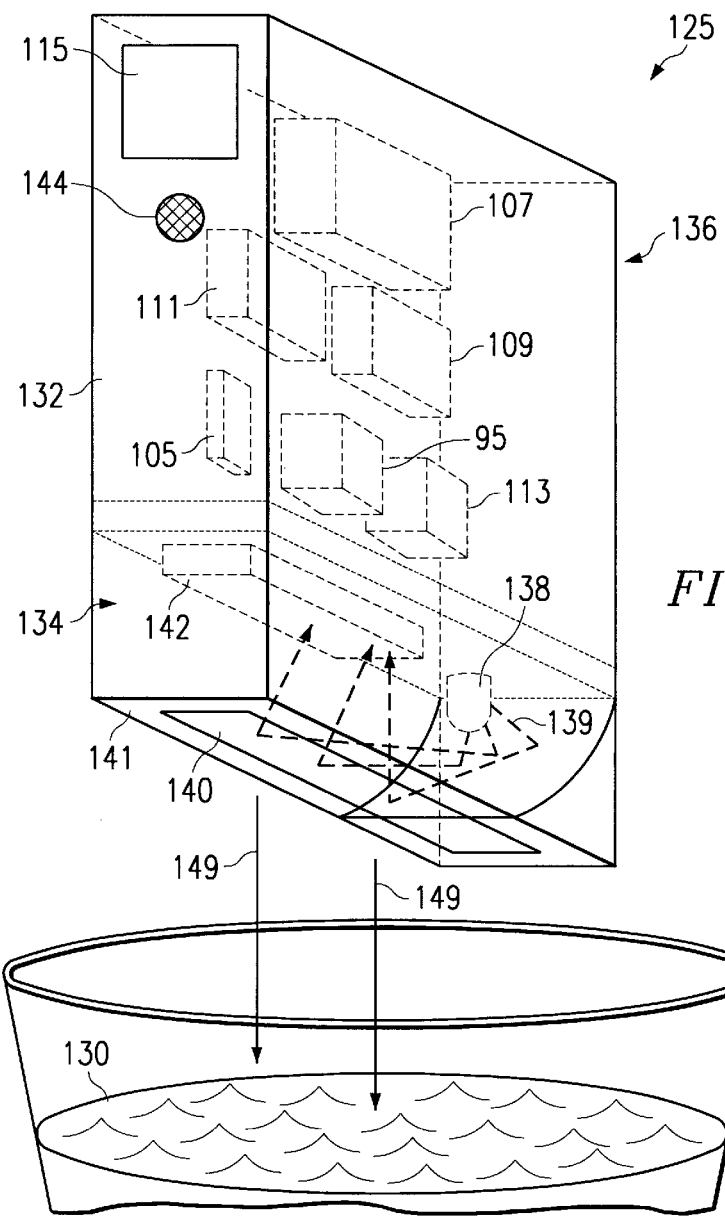
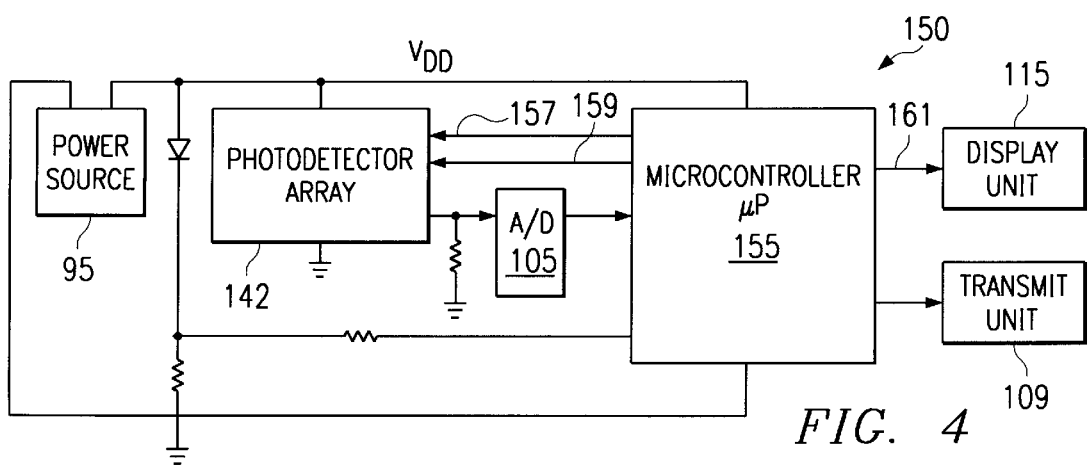

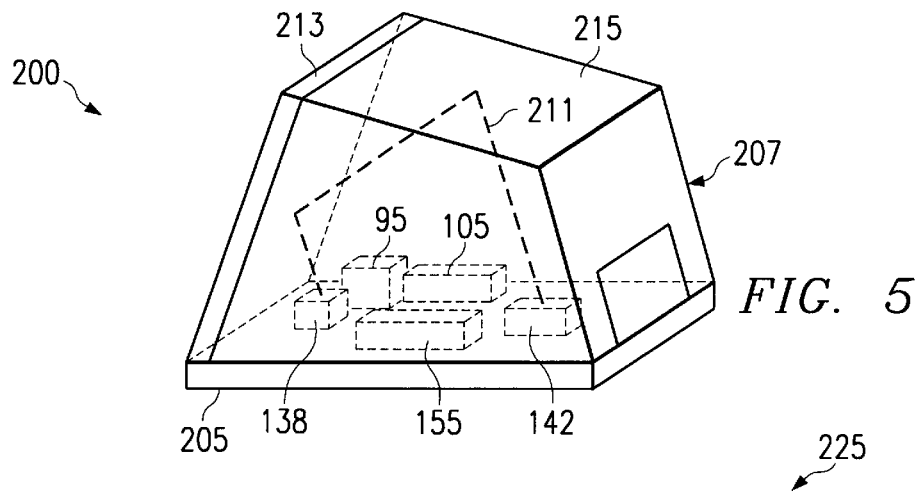
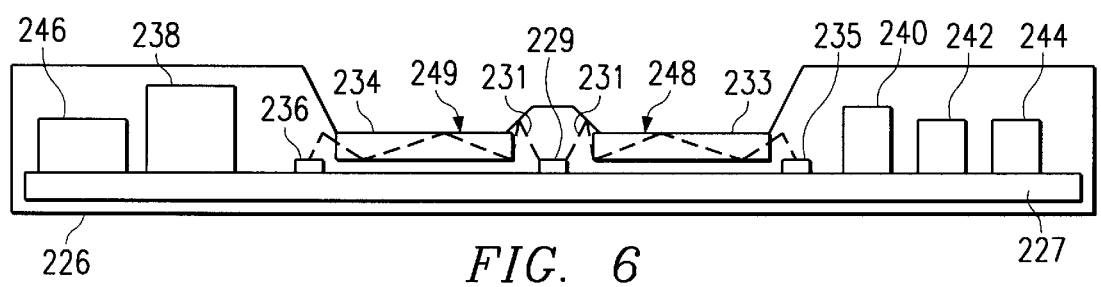
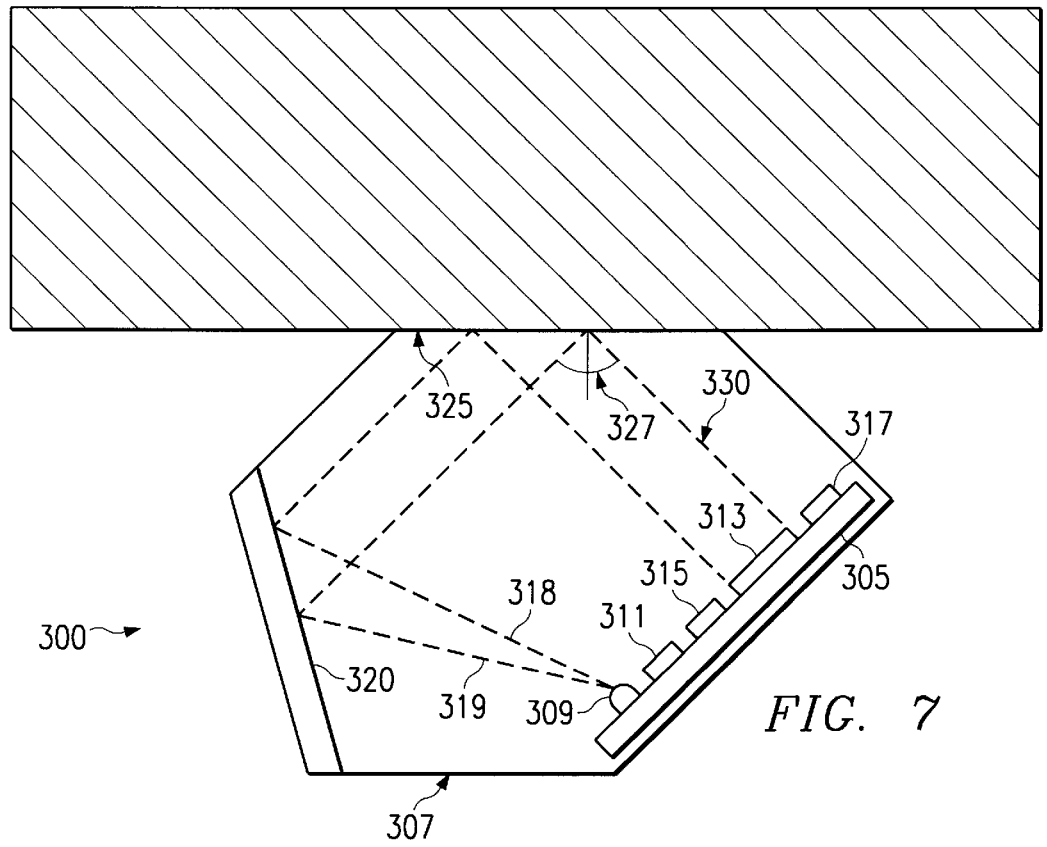

SELF-CONTAINED OPTICAL SENSOR SYSTEM

This application claims priority under 35 USC §119(e)(1) of provisional application No. 60/026,760 filed Oct. 1, 1996.

TECHNICAL FIELD OF THE INVENTION

The present invention relates in general to optical sensors and in particular to an integrated chemical-optical sensor system that detects the presence of materials used in the fields of chemical, biochemical, biological or biomedical analysis, process control, pollution detection and control, and other similar areas.

BACKGROUND OF THE INVENTION

Without limiting the scope of the invention, its background is described in connection with an optical sensor system that may be used to detect the presence of a given sample of interest such as a gas, a liquid or solid.

The use of fluorescence and surface plasmon resonance based technology to detect sample gases and liquids is known by those skilled in the art. A typical application of the fluorescence based sensing involves the molecular labeling of a thin film, cable, or other article, followed by excitation and fluorescent measurement in the presence of the particular sample of interest. Fluorescent labeling involves the deposition of a suitable fluorescent chemistry known to interact with the sample.

A source of excitation light is directed at the coated article, resulting in an emission light. Direct contact with the sample effects changes in the character of the emission light. A spectrograph or other similar instrument can be used to measure the emission thus indicating the presence and concentration thereof.

In surface plasmon resonance based sensing, a source of electromagnetic radiation (light) strikes a thin conducting layer and is partially reflected toward an array of radiation detectors. The light internally reflected by the conducting layer has a minimum intensity at a particular angle referred to as the resonance angle. Therefore, the radiation detector having the minimum output level is associated with the light rays that have reflected off the conducting layer at the resonance angle, which is a function of the refractive index of the ambient sample. By detecting the angle at which resonance occurs, the refractive index may be determined and used to identify the sample.

One limitation of the prior art sensor systems is that they are not fully integrated; most are interfaced with equipment such as a personal computer or hand held instrument to perform measurement and analysis. Furthermore, chemical sensing by optical means often requires the exposure of a sensor surface to the ambient under test. While the electro-optic components may be protected, the connector pins remain exposed. In many applications, however, protecting the electro-optic components and electrical connections is critical such as in liquid-based applications which may require submersion of the sensor into the sample.

Also, the separate and additional circuitry used to interface the prior art sensors to remote processing systems increases total system cost and maintenance.

What is needed is a sensor system that integrates the electro-optic components in a self-contained package. A system that permits the wireless transfer of data to a personal computer or other processing platform would have great advantages over the prior art systems. The present invention solves the aforementioned problems by incorporating the necessary system elements within a self-contained sensor package.

SUMMARY OF THE INVENTION

Prior art sensors and sensor systems are not integrated and as such have limited use in most field applications. Accordingly, it is a primary object of the present invention to provide a self-contained sensor system for use in most field applications. A self-contained sensor embodied in a package that does not require external physical connections is disclosed. The package includes an onboard power supply making the sensor portable and more compact by eliminating the physical connections to an external power supply.

Another object of the present invention is to eliminate the separate and additional interface electronics associated with prior art sensor systems. The present invention has onboard signal processing and can provide meaningful data via an integrated display.

Yet another object of the present invention is to provide a low cost sensor device that can be manufactured in high volume.

Generally, and in one form of the invention, a light source powered by a self-contained power supply emits electromagnetic radiation onto a chemically coated conductive layer on a protective optical housing. The light is internally reflected into a self-contained photodetector which can resolve and measure the light. Data from the photodetector is converted into digital format and relayed to an integrated signal processing circuit. Since all system components are enclosed within a protective light transmissive optical housing, the unit is self-contained and independent of any external system(s).

In another embodiment, onboard communications features are included in the housing providing transmit and receive capabilities for the sensor for wireless communications with a remote processing system. The communications medium may be any wireless means including infrared, radio frequency, or a combination thereof. In another embodiment, a display is included in the sensor system and provides immediate visible feedback relating to the subject material or functional aspect of the sensor such as the power-on state and battery level. In yet another embodiment, a microcontroller is included onboard having an interface to the various sensor components such as the photodetector, the receiver and transmitter and signal processor. Also, an analog-to-digital converter may also be included.

An advantage of the present invention is that it eliminates the need for separate interface electronics. The sensor is self-contained and, thus, it may be safely exposed to the ambient material under test. This is particularly significant in applications which may require the submersion of the sensor into a liquid. Another advantage of the invention is its small size, allowing the device to be employed in a large number of applications.

For a more complete understanding of the present invention, including its features and advantages, reference is now made to the following detailed description, taken in conjunction with the accompanying drawings.

BRIEF DESCRIPTION OF THE DRAWINGS

In the drawings:

FIG. 3 is a perspective view of a self-contained sensor system according to a second embodiment of the invention;

FIG. 4 is a schematic diagram illustrating the internal arrangement of components for one embodiment of the invention;

FIG. 5 is a perspective view of a third embodiment of the invention;

FIG. 6 is a cross sectional view an integrated sensor having a light transmission configuration in accordance with the invention; and FIG. 7 is a cross sectional view an integrated sensor having a surface plasmon resonance configuration in accordance with the invention;

Corresponding numerals and symbols in the different figures refer to corresponding parts unless otherwise indicated.

DETAILED DESCRIPTION OF THE PREFERRED EMBODIMENT

Figure 1:
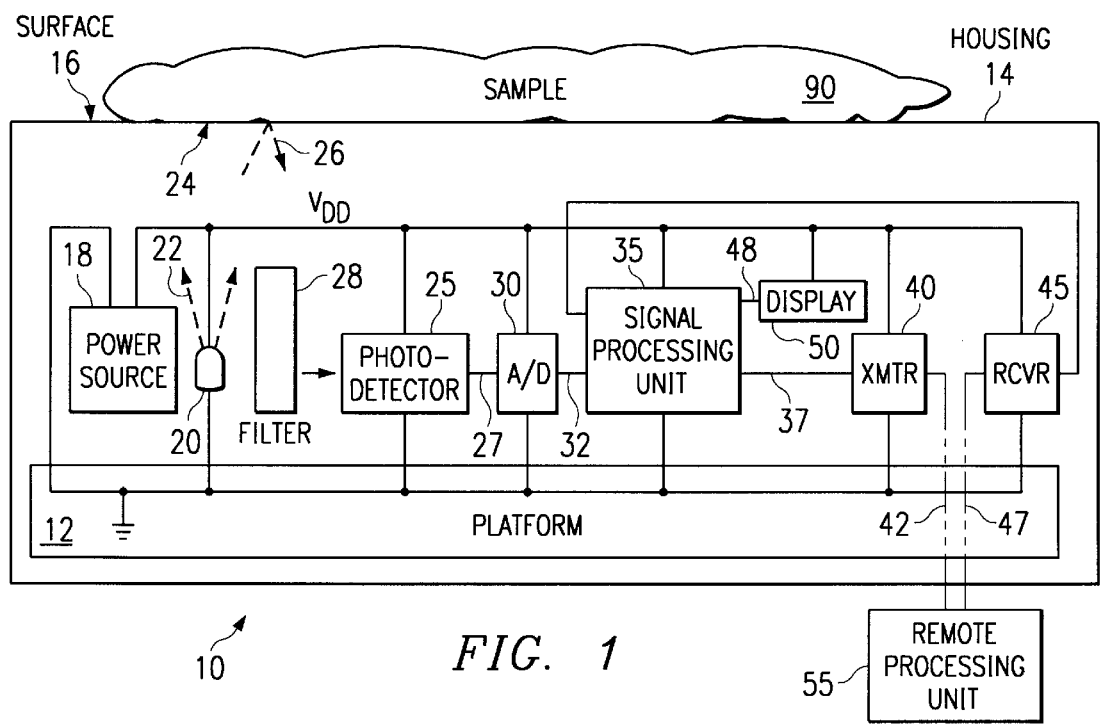
FIG. 1 is a block diagram of a self-contained optical sensor in accordance with the invention.

In reference to FIG. 1, a functional block diagram of a self-contained optical sensor system in accordance with one embodiment of the invention is shown and denoted generally as 10. Sensor system 10 has a platform 12 to which the various system components are connected. An encapsulating housing 14 extends over the platform 12 and forms a light transmissive formation over the various device components. As shown, housing 14 has at least one surface 16 in contact the sample 90.

In one embodiment of the invention, platform 12 is made of a dark, light-absorbing material, such as a hard resin or epoxy, although other materials may be used. The specific material depends primarily on the cost of manufacturing and, as such, could include material such as glass, PCB, ceramic, or a suitable lead frame such as copper, steel, an alloy, or other plated material. Also, the platform 12 may be coated with a light-absorbing material such as black epoxy or a thin resin layer.

Preferably, housing 14 is made of an encapsulant material having a light transmissive quality transparent to light wavelengths of interest and is bonded to a surface of the platform 12.

Being a self-contained system, a power source 18 is provided and operably coupled to the various active components, such as light source 20, photodetector 25, A/D converter 30, signal processing unit 35, transmitter 40 and receiver 45. Power source 18 may be a Ni-cad or lithium cell battery, charged capacitor or other readily available source of energy to supply operational current via the line $V_{DD}$ to the active components of system 10. GND line provides a signal point of reference.

As shown, at least one light source 20 is operably coupled to power source 18. Light source 20 may be a light emitting diode (LED), laser diode, filament, or any other suitable source of electromagnetic radiation providing the system 10 with a source of excitation light energy 22, which, due to the optically transmissive properties of enclosure 14, travels throughout the enclosure 14.

The emitted excitation light 22 travels within the interior of enclosure 14 and impacts surface 24 of housing 14, resulting in emission energy 26. As is known by those skilled in the art, energy 26 results from the molecular interaction of the chemistry coat on outer surface 16 with the sample of interest 90. Thus, the exterior surface 16 is coated with a fluorescence based chemical layer known to interact with sample 90 to create a measurable change in emission 26. The particular type of fluorescence coat used depends on the sample 90 and on numerous other variables which are well known in the art. The excitation light 22 is used as a catalyst to the fluorophore coated surface 16, and when sensor system 10 is placed in contact with sample 90, causes changes in emission energy 26.

An optional optical filter 28 allows the relevant frequency spectrum of emission energy 26 to pass on to photodetector 25. In this way, the emission energy 26 is separated from the stray sources of excitation energy 22 allowing signal wavelengths indicative of sample 90 to reach the detector 25. As such, the filter 28 increases sensor sensitivity and makes it less susceptible to noise caused by other radiation sources. An interference filter, the W.P.-400-500-25 manufactured by Infrared Engineering, may be used for this purpose.

Photodetector 25 is spatially arranged within housing 14 to receive emission energy 26 resulting from the interaction of the fluorophore and the sample 90. In various embodiments, photodetector 25 is a single element light-to-voltage or a light-to-frequency detector such as the TSL250 or TSL230, respectively. In other embodiments, an n x 1 linear array of n detector pixels, such at TSL214, TSL215, or TSL218 is used.

As shown, photodetector 25 is communicably coupled to an analog-to-digital (A/D) converter 30 via interface 27 which can be an address data bus or other similar communications paths allowing the exchange of data between the photodetector 25 and the A/D converter 30. Thus digital bitstream data can be processed and transformed into its analog signal equivalent, which is processed further by signal processing unit 35, shown coupled to A/D converter 30 via interface 32.

It should be understood that A/D converter 30 and signal processing unit 35 may be integrated into a single digital signal processor of the type commonly and readily available in the industry. As can be appreciated by those skilled in the art, signal processing unit 35 is preprogrammed to analyze and characterize the occurrence and timing of emission energy 26 and therefore derive meaningful information about the sample 90.

Various sample results may be obtained. For example, signal processing unit 35 can be configured to determine the total amount of time that sample 90 is within a given proximity of the sensor system 10 or the frequency of occurrence over a given period of time. Other sample 90 results may be obtained and are contemplated by the invention.

A display 50 is operably coupled to signal processing unit 35 via interface 48 allowing a visual readout or measurement indicative of the sample data. A liquid crystal display or single LED are suitable display 50 components but others may be used. Likewise, signal processing unit 35 is operably coupled to transmit circuit 40 via interface 37 for the transmission of sample data to a remote processing unit 55. The transmitter 40 subsystem may be implemented using various devices including a radio frequency (RF) transmitter, infrared signal transmitter, or other similar communications means allowing wireless communications between sensor system 10 and the remote processing unit 55. Transmit path 42 is shown linking sensor system 10 to remote processing unit 55. Since wireless communications is preferred, path 42 is air, water or some other nonconductive pathway.

Also shown in FIG. 1 is a receive circuit 45, which allows sensor system 10 to obtain signals and/or commands from remote processing unit 55. For example, the remote processing system 55 can activate and deactivate sensor system 10 causing light source 20 to emit light during selected time periods. If so configured, receiver 45 is operably coupled to the signal processing unit 35 via pathway 47, allowing remote processing unit 55 to control the various functions of sensor system 10.

In one form of the invention, sensor system 10 is a completely integrated detector with a life span roughly equal to that of power source 18. Thus, a replaceable, disposable sensing device which can be placed inside a hand-held portable instrument or other similar device is contemplated.

FIG. 1 is a block diagram for an integrated self-contained sensor according to the invention. By encapsulating the various functional system components within housing 14 along with the required transmit 40 and receive 45 capabilities, a self-contained sensor system 10 is defined which does not require external pins for connection. The sensor system may take the form of a miniaturized capsule such as that depicted in FIG. 2. The remote communications may occur by optical, infrared or radio frequency means or a combination thereof. Likewise, any other means not requiring external physical connections may be used.

Figure 2:
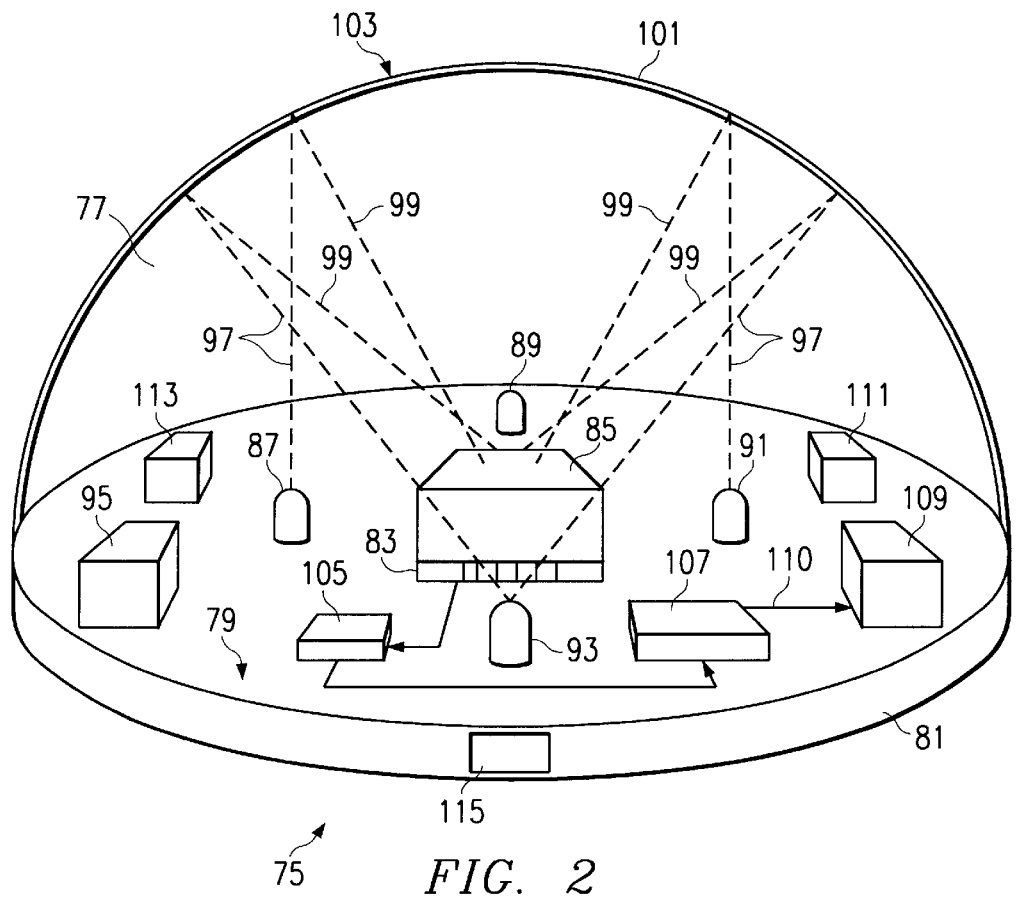
FIG. 2 is a perspective view of a self-contained sensor according to one embodiment of the invention.

Turning now to FIG. 2, a specific embodiment of a self-contained sensor in accordance with the invention is shown and denoted generally as 75. A hemispherical dome-shaped housing 77 extends from the upper surface 79 of platform 81. Housing 77 forms an encapsulating structure surrounding platform 81.

As shown, photodetector 83 is coupled to the upper surface 79 about a substantially central location of the platform 81. A suitable photodetector 83 is a light-to-voltage or light-to-frequency converter, such as the TSL250 or TSL230, respectively, in which light energy striking a pixel generates electron-hole pairs in the region under the pixel. The field generated by the bias on the pixel causes the electrons to collect in the element while the holes are swept into the substrate. The photodetector 83 thereby produces an output signal with a voltage proportional to the intensity of the radiation energy striking the photodetector 83.

Directly overlying photodetector 83 is filter 85 which blocks light from the receiving face of photodetector 83 outside a certain wavelength spectrum. Four (4) light sources 87, 89, 91 and 93 are coupled to the upper surface 79 surrounding the photodetector 83 at substantially equidistant positions from the center of the platform 81 and symmetrically arranged about and within the housing 77.

A power source 95 is also coupled to the upper surface 79 and operably coupled to the various active components of the sensor 75 including photodetector 83, light sources 87, 89, 91 and 93 among others. Power source 95 provides power to all the electro-optical components within the housing 77 allowing the sensor 75 to operate without an external link to an outside source of power.

Light emissions 97 and 99 illustrate the operational aspects of the sensor 75. Light 97 from light sources 87, 89, 91, and 93 incident to upper surface 79 of the filter 85 and the platform 81 where it is absorbed. The fluorescent chemistry 103 on surface 101 interacts with the ambient sample (not shown) and produces a charge in the fluorescence emission which travels toward the photodetector 83. The light absorbent filter 85 blocks out unwanted energy wavelengths which are outside the emission spectra of interest.

The A/D converter 105 receives an analog signal from photodetector 83 producing a corresponding digital output signal for digital storage and analysis. A/D converter 105 is coupled to upper surface 79 of the platform 81 and embedded within housing material 77. Likewise, signal processing circuit 107 is coupled to platform 81 and communicably interfaced to the A/D convertor 105 to receive the output digital signal relating to the sample in question.

Transmit circuit 109 and receive circuit 111 are provided permitting wireless communications between the sensor 75 and an external processing system where the light data can be further analyzed. For example, the transmit circuit 109 can receive digital data from the signal processing circuit 107 and relay it to the remote processing system via path 110. Likewise, the receive circuit 111 receives commands, parameters and other sample related instructions from a remote source which, in turns, relays that information to signal processing circuit 107. A driving circuit 113 is provided to control the communications protocol and for handshake between the transmit circuit 109, the receive circuit 111 and the external processing system.

Data from signal processing circuit 107 may be sent to a display 115 which is visible from the exterior of the sensor 75. The display 115 provides visual feedback to the user indicative of the sample under test. In this regard, various display types can be employed. For example, display 115 can be a single light emitting mode which lights up in the presence of the sample. Those of skill in the art will recognize that the elements and components of sensor 75 as illustrated may be rearranged about platform 81 and housing 77 and still be within the spirit and scope of the invention.

Turning now to FIG. 3, an alternative embodiment of a sensor 125 which is suitable for immersion in a liquid sample 130 of interest is shown. A substantially rectangular and box-shaped enclosure 132 is waterproof and used to the house the sensor 125 components. Enclosure 132 has a bottom 134 which provides the platform to which the sensor 125 components are affixed. The light source 138 emits light 139 which reflects off mirrored surface 140 and strikes sensor surface 142.

In one embodiment a Surface Plasmon Resonance ("SPR") layer is formed on surface 140 of the exterior of enclosure 132. A SPR layer, which, as known in the art, comprises a thin layer of a conductive material such as copper, silver or gold, having a substantially uniform thickness which may vary from about 200 Å to about 600 Å and still permit surface plasmon resonance to occur. The specific film thickness is determined by experimentation with respect to the frequency of the radiation for the light source 138 and the properties of the conductive material used for the layer.

As known in the art, when radiation strikes a thin conductive film at the interface of an insulator, the intensity of reflection therefrom is a function of the angle of incidence of the radiation onto the film and the refractive index of the material in contact with the other side of the film. Hence, by determining the angle at which minimum reflectance occurs, it is possible to determine the index of refraction of the liquid sample 130 on the side of the film opposite the side the radiation is reflected from.

An analog signal from the photodetector array 142 is converted into a digital signal by A/D converter 105. The sensor 125 includes all necessary electro-optical components wired to a circuit board (not shown). In one embodiment of the invention, these components include A/D converter 105, power source 95, driving circuit 113, signal processing circuit 107, transmit circuit 109, and receive circuit 111.

Thus, when the sensor 125 is immersed 149 in liquid sample 130 the reflected signal is detected by the detector array 142. Depending on the particular array 142 used, either a voltage or frequency output related to the sample 130 is obtained which, in turn, is relayed to A/D converter 105 via an internal path (not shown). The digital output from A/D converter 105 is then relayed to signal processing circuit 107 which is programmed to analyze the data. The presence of the sample 130 may be indicated to the user on display 115.

As with the sensor configuration 75 of FIG. 2, the transmit circuit 109 has the ability to communicate via a wireless interface 144 with a remote system for sample data downloads. Receive circuit 111 has the capability of receiving information from the remote system via interface 144. Means for transmitting and receiving information through interface 144 may include optical, infrared, radio frequency, or other means not requiring external physical connections, or a combination thereof. Power source 95 supplies power to all electrical components enclosed in the sensor 125. In use, the sensor 125 is positioned such that the sensor surface 141 is in direct contact with a sample 130.

Those of skill in the art will recognize that the components and elements illustrated in FIG. 3 may be rearranged while maintaining equivalence in function according to the invention.

Further alternative designs are possible. For example, in yet another embodiment, a microcontroller circuit 150 is included on board within the enclosure 132. This arrangement is illustrated in FIG. 4 wherein a schematic circuit diagram 150 illustrating the placement of components according to one embodiment is shown. Microcontroller 155 provides clock and serial input signals to photodetector array 83 via interfaces 157 and 159, respectively. A suitable microcontroller is the MC68705, but others may be used. In the SPR configuration, photodetector 83 is replaced with a photodetector array 142 such as TSL213. The clock 157 controls charge transfer, pixel output, and reset for the sensor 150 while serial input 159 defines the end of the integration period and initiates the pixel output sequence.

Microcontroller 155 transmits data to display unit 115 via interface 161. One form of display 115 is a multi-digit LED display indicating whether or not the sample is present. Another display 115 is a LCD which is capable of alpha-numeric output. Information from microcontroller 155 includes the line-pixel position or light/dark transition count of the detector 142. Output from microcontroller 155 may also be directed to a transmit unit 109 where it may be used to determine further information about the sample beyond the information revealed in display 115.

It should be understood that many device configurations may be employed to achieve a self-contained sensor according to the invention. FIGS. 5, 6, and 7 depict three variations of the invention. For example, in FIG. 5 an SPR sensor 200 configuration of the invention is shown. The platform 205 is enclosed in housing 207 which has a light transmissive quality. As with the other sensor configurations 10, 75, and 125, the electro-optic components, such as the light source 138, power source 95, microcontroller 155, A/D converter 105, and photodetector array 142, are operably coupled to each other and to platform 205 and embedded within encapsulating housing 205. The housing 207 has a substantially trapezoidal shape with has advantages understood by those skilled in the art.

In another embodiment, a power supply watchdog circuit is integrated in the sensor system and operates to turn ON the device in the presence of the sample. The power supply watchdog circuit, as known in the art, would simply include a resistive element and a light emitting diode connected in series from the line $V_{DD}$ to ground GND.

In operation, light 211 travels within housing 207 source 138 reflects off mirrored surface 213. The reflected light strikes the sensing surface 214 where it is reflected and becomes incident on photodetector array 142. The exterior of sensing surface 214 is coated with an SPR layer that interacts with the sample to alter the refractive index of light 211 formed at the surface 214 sample interface.

In FIG. 6 a light transmission sensor configuration 225 is shown. A sensor 225 is a self-contained light transmission device having a platform 227 with at least one light source 229 which generates a light signal 231 optically coupled via light guides 233 and 234 towards photodetectors 235 and 236. An encapsulating housing 226 surrounds the platform 227 and other components of the sensor 225 providing a rugged and self-contained unit.

As with one other configuration, sensor 225 has an onboard power source 238, signal processing unit 240, transmit circuitry 242, receive circuitry 244 and display 246 all encapsulated within housing 226. At least one of the light guides 233 or 234 is coated with a chemical layer known to interact with a sample of interest.

As shown, at least one light source 229 is positioned about platform 227 within housing 226. The photodetectors 235 and 236 are coupled to the platform 227 on either side of light source 229 and disposed to receive light 231 traveling through light guides 233 and 234, respectively. When the sample of interest comes in contact with surfaces 248 and 249, the refractive index of the interface is measurably altered.

In FIG. 7, a self-contained critical angle sensor system 300, in accordance with still another embodiment of the invention is shown. All the electro-optic components are coupled to platform 305 and contained in housing 307. At least one light source 309, power supply 311, photodetector 313, signal processing unit 315, and transmit circuitry 317 are encapsulated in housing 307 which as shown has a five-sided polygonal shape. As with other embodiments of the invention, the light source 309 emits light rays 318 and 319 toward mirrored surface 320. Light rays 318 and 319 travel through and reflect off surface 320 and strike sample-sensor interface 325 at a range of angles.

With sensor 300, the critical angle 327 is the angle measured between the incident light ray 330 and the normal to the sample-sensor interface 325. For angles of incidence larger than the critical angle 327, the incident ray 330 is totally internally reflected within housing 307, with no refracted component, and its full intensity is therefore directed toward photodetector 313. This total internal reflection can only occur when light originates in a medium of a higher index of refraction as compared to the sample.

A suitable photodetector 313 is a single element light-to-voltage or a light-to-frequency detector such as the TSL250 or TSL230, respectively, or a linear array of resolution n×1, consisting of n discrete photosensing areas, or pixels, such as the TSL214, TSL215, or TSL218. With an array, light energy striking a pixel generates electron-hole pairs in the region under the pixel. The field generated by the bias on the pixel causes the electrons to collect in the element while the holes are swept into the substrate. Each sensing area in the array thereby produces a signal on an output pin with a voltage that is proportional to the intensity of the radiation striking the photodetector. This intensity and its corresponding voltage are at their maxima in the total internal reflection region.

As described, a range of angles of the reflected light rays are projected onto the photodetector 313. The critical angle is marked by a transition on the array from high to low. Signals from the photodetector 313 are transmitted within enclosure 9 to signal processing unit 35. Also, signal processing unit 315 may provide input signals such as clock and serial input for photodetector 313. Signal processing unit 315 may be used so that the sensor resolution may be higher than the detector pixel resolution.

Signal processing unit 315 may be preprogrammed to analyze and characterize the intensity, occurrence and timing of light rays and therefore calculate other meaningful information about the sample 60. For example, signal processing unit 315 can be preprogrammed to determine the total amount of time that sample 60 is in contact with sensor system 300. Also, signal processing unit 315 can be preprogrammed to determine the frequency of occurrence of sample 60 over a given period of time. Other results are contemplated and within the scope of the invention.

Output data from signal processing unit 315 may be transmitted via transmit circuitry 40. Transmit circuitry has the capability of communicating via a wireless means to a secondary system, such as a computer, hand-held meter, calculator, printer, logic analyzer, or other similar system.

Those of skill in the art will recognize that the elements illustrated in FIG. 7 can be moved or relocated while still retaining equivalence within the scope of one invention as herein described. The various sensor configurations disclosed including surface plasmon resonance, fluorescence, light or transmission, and critical angle are all examples of sensor application which benefit from the present invention. As such, various modifications of the illustrative embodiments as well as other embodiments of the invention will be apparent to persons skilled in the art upon reference to the description and it is, intended that the appended claims encompass any such modifications or embodiments.

What is claimed is:

1. A self-contained optical sensor system comprising:
    a platform having an upper surface and a bottom surface;
    at least one light source coupled to said upper surface of said platform;
    at least one photodetector coupled to said upper surface of said platform adjacent said light source;
    a power supply operably coupled to both said light source and said photodetector; and
    an encapsulating housing extending from and over said platform about said upper surface and having a surface predisposed to receive light from said light source and direct it towards said photodetector, wherein said power supply is arranged within said encapsulating housing.

2. The system as recited in claim 1 further comprising a layer of electrically conductive material extending over a portion of said housing surface.

3. The system as recited in claim 1 further comprising a fluorescence based chemical coat deposited on a portion of said housing surface.

4. The system as recited in claim 1 further comprising a surface plasmon resonance based chemical coat deposited on a portion of said housing surface.

5. The system as recited in claim 1 wherein said at least one photodetector comprises an n x 1 array of photodetector cells.

6. The system as recited in claim 5 wherein said system has a critical angle sensor configuration and wherein a plurality of light rays reflect off said housing surface in the direction of the n×1 array of photodetector cells.

7. The system as recited in claim 1 further comprising an A/D converter coupled to said upper surface of said platform and operably coupled to said photodetector.

8. The system as recited in claim 7 further comprising a signal processing circuit coupled to said upper surface of said platform and operably coupled to said A/D converter.

9. The system as recited in claim 8 further comprising a display visibly arranged within said housing and electronically connected to said signal processing circuit.

10. A self-contained optical sensor for detecting the presence of a given sample of interest, said sensor comprising:
    a platform having an upper surface coated with a light absorbing substance;
    a plurality of light sources coupled to said platform at uniformly spaced positions about said upper surface;
    a photodetector coupled to said upper surface of said platform adjacent said light sources;
    a power supply operably coupled to both said light sources and said photodetector;
    an A/D converter circuit coupled to said upper surface of said platform and having an input interface to said photodetector and an output;
    a signal processing circuit coupled to said output of said A/D converter circuit; an encapsulating housing extending from and over said platform about said upper surface and having a surface predisposed to receive light from said light sources and direct it towards said photodetector, said surface having a chemical coat deposited thereon, wherein said power supply is arranged within said encapsulating housing;
    a display visibly arranged within said housing and electronically connected to said signal processing circuit; and
    transmit and receive circuits embedded within said housing and having an interface electronically coupled to said signal processing circuit, said transmit and receive circuits operating on a wireless communications basis.

11. The system as recited in claim 10 wherein said chemical coat is a surface plasmon resonance based layer covering a portion of said housing surface.

12. The system as recited in claim 10 wherein said photodetector comprises an n×1 array of photodetector cells.

13. The system as recited in claim 10 wherein said housing has a hemispherical shape.

14. The system as recited in claim 10 further comprising a light absorbent filter directly overlying said photodetector.

15. The system as recited in claim 1 wherein said light sources are light emitting diodes.

16. A self-contained optical sensor for detecting the presence of a material sample, said sensor comprising:
    a platform;
    a light emitting diode coupled to said platform;
    an light transmissive housing extending from platform, and forming an encapsulant with a chemically coated outer surface, said housing enclosing said light emitting diode;
    a photodetector affixed to said platform within said housing and arranged to receive light reflected from said outer surface of said housing;
    an analog-to-digital converter circuit affixed to said platform within said housing and having an input coupled to said photodetector and an output;
    a signal processing circuit affixed to said platform within said housing adjacent said analog-to-digital converter circuit and electronically connected to said output;
    a wireless communications means affixed to said platform within said housing and coupled to said signal processing circuit.

17. The sensor according to claim 16 further comprising:
    a display coupled to said signal processing unit, said display visibly arranged about the outer surface of said housing; and
    and onboard power source coupled to said light source, said photodetector, said signal processing circuit and said wireless communication means, said power source arranged within said housing.

18. The sensor according to claim 16 wherein said outer surface of said housing is coated with a surface plasmon resonance layer.

* * * * *